United States Patent [19]

Culbert

[11] Patent Number: Plant 5,367

[45] Date of Patent: Dec. 11, 1984

[54] CHRYSANTHEMUM PLANT NAMED—ILLINI WINDMILL

[75] Inventor: John R. Culbert, Clinton, Ill.

[73] Assignee: University of Illinois, Chicago, Ill.

[21] Appl. No.: 488,073

[22] Filed: Apr. 25, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Illini Windmill characterized by its flat capitulum form and single anemone capitulum type, white ray florets and yellow-green to bright yellow disc florets, 60–70 mm. across face of capitulum, short and compact growth and semi-upright branching patterns, excellent flower form and color, and by its long shelf life.

1 Drawing Figure

The present invention comprises a new and distinct cultivar of *Chrysanthemum morifolium,* Ramat., hereinafter referred to by the cultivar name Illini Windmill.

Illini Windmill is a product of a planned breeding program which had the objective of creating new chrysanthemum cultivars with single anemone capitulum type, white ray florets and bright yellow disc florets, 9 week response, and the ability to produce acceptable quality in a year round pot mum program. Such traits in combination were not present in previously available commercial cultivars.

Illini Windmill was originated from a hybridization made in a controlled breeding program in Urbana, Ill. in 1975. The female parent was identified as 24-02-71, and the male parent as 11-06-71. Illini Windmill was discovered and selected as one flowering plant within the progeny of the selected parentage by John R. Culbert in July 1976 in a controlled environment in Urbana, Ill., and subsequently given the code name FP ILL-75-1-WS.

The first act of asexual reproduction of Illini Windmill was accomplished when vegetative cuttings were taken from the initial selection on October 1976 in a controlled environment in Urbana, Ill. by a technician working under formulations established and supervised by John R. Culbert. Horticultural examination of selected units initiated Mar. 29, 1977 has demonstrated that the combination of characteristics as herein disclosed for Illini Windmill are firmly fixed and are retained through successive generations of asexual reproduction.

Illini Windmill has not been observed under all possible environmental conditions. The phenotype may vary significantly with variations in environment such as temperature, light intensity, and day length. The following observations, measurements and comparisons describe plants grown in Urbana and West Chicago, Ill. and Parrish, Fla., under greenhouse conditions which approximate those generally used in commercial practice.

The following traits have been repeatedly observed and are determined to be basic characteristics of Illini Windmill, which in combination distinguish this chrysanthemum as a new and distinct cultivar:

1. Flat capitulum form, with the ray florets being broad with rounded tips; the disc florets form a small well defined rounded cushion.

2. Single anemone capitulum type.
3. The anemone disc florets are more developed and pronounced under certain conditions. Under high temperatures they are smaller and less pronounced than under low temperatures.
4. White ray florets.
5. Bright yellow disc florets (mature) to yellow-green (immature).
6. Diameter across face of the capitulum 60–70 mm.
7. Short pot plant height of about 200 mm. from edge of pot.
8. Semi-upright branching habit.
9. Excellent flower form and color results in a very showy plant.
10. Exceptionally long shelf life.

Of the many commercial cultivars known to the present inventor, the most similar in comparison to Illini Windmill is Frosty, the characteristics of which are disclosed in the pending application of Peter S. Hesse and Leonard H. Shoesmith. Reference is made to attached Chart A which compares certain characteristics of Illini Windmill to those same characteristics of Frosty.

The accompanying photographic drawings show typical inflorescence and foliage characteristics of Illini Windmill, with colors being as nearly true as possible with illustration of this type.

In the following description color references are made to The Royal Horticultural Society Colour Chart. The color values were determined between 3:30–4:30 P.M. on Nov. 16, 1982 under 2000–5000 foot candles at Parrish, Fla.

CLASSIFICATION

Botanical: *Chrysanthemum morifolium,* Ramat., cv Illini Windmill.

Commercial: Spray pot grown pinched and not disbudded.

INFLORESCENCE

Capitulum:

*Form.*—Flat; normally 2 but occasionally 4 rows of broad ray florets with rounded tips; rays range from 30–65 in number depending on season and culture, mostly 40–50 in number; smooth, well defined rounded cushion of disc florets.

*Type.*—Single anemone.

*Diameter across face.*—60–70 mm.

*Number.*—Normally 10 to 12 flowers per plant as sprays on pinched plants; number can vary from 8 to 25 depending on season and culture.

Corolla of ray florets:

*Color (general tonality from a distance of three meters).*—White, with no pinking of flowers on maturity, as observed to date.

*Color (abaxial).*—155B.

*Color (adaxial).*—155B.

Corolla of disc florets:

*Color (mature).*—9A.

*Color (immature).*—150A.

Reproductive organs:

*Androecium.*—Present in disc florets only — many.

*Gynoecium.*—Present in both ray and disc florets — many.

PLANT

General appearance:

*Height.*—About 200 mm.

*Appearance.*—Medium short, compact and semi-upright.

Foliage:

*Color (abaxial).*—147B.

*Color (adaxial).*—147A.

*Shape.*—Ovate, deeply lobed and serrate.

Response: Varies between 8 and 9 weeks depending on season and culture; fastest in March through October.

CHART A

| | ILLINI WINDMILL | FROSTY |
|---|---|---|
| Diameter across face of capitulum | 60–70 mm. | 34–45 mm. |
| Ray floret color | white | white |
| Disc floret color | Bright yellow | Pale Yellow |
| Flower type | Anemone | Anemone |
| Plant height | 180–230 mm. | 200–250 mm. |
| Flower response | 8–9 weeks | 9 weeks |
| Leaf shape | Ovate | Elliptical |

I claim:

1. A new and distinct cultivar of chrysanthemum plant named Illini Windmill, as described and illustrated, and particularly characterized by its flat capitulum form and single anemone capitulum type, white ray florets and yellow-green to bright yellow disc florets, 60–70 mm. across face of capitulum, short and compact growth and semi-upright branching patterns, excellent flower form and color, and by its long shelf life.

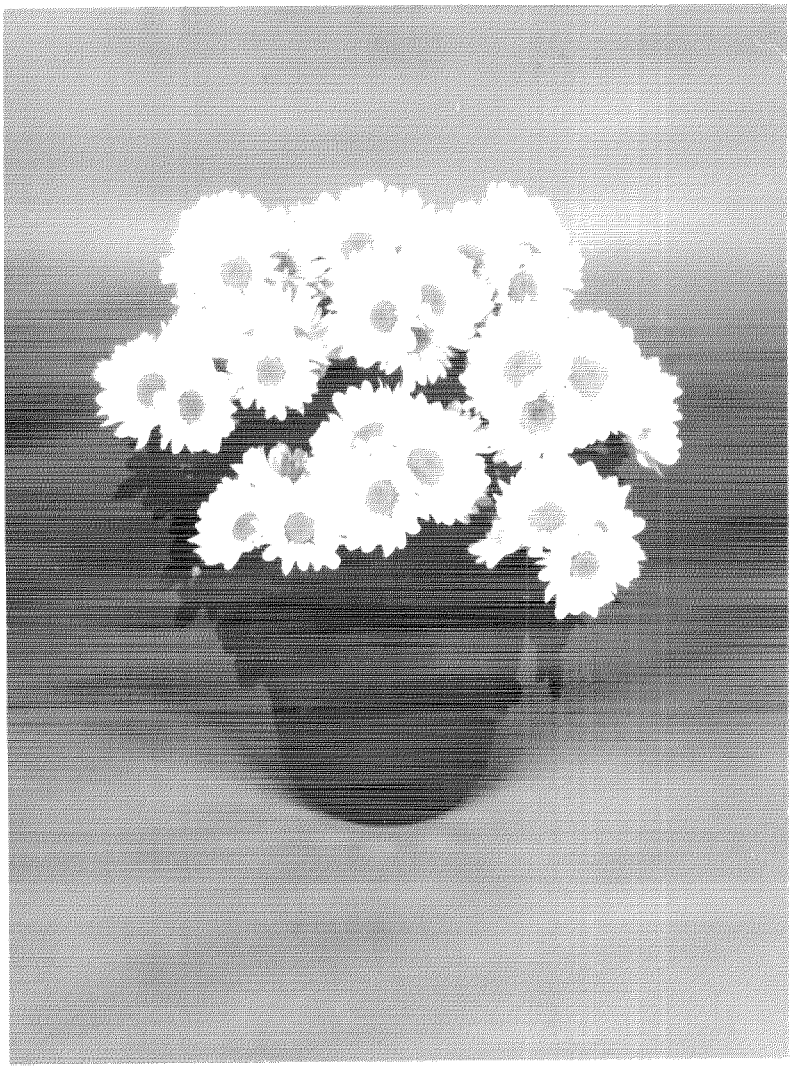

* * * * *